United States Patent [19]

Leacock

[11] 4,147,721
[45] Apr. 3, 1979

[54] PROCESS FOR RECOVERING METHACRYLIC ACID
[75] Inventor: James Leacock, New York, N.Y.
[73] Assignee: Halcon Research and Development Corporation, New York, N.Y.
[21] Appl. No.: 894,062
[22] Filed: Apr. 6, 1978
[51] Int. Cl.² .................. B01D 3/36; C07C 57/04; C07C 51/42
[52] U.S. Cl. .................. 562/532; 203/42; 203/62; 203/63; 203/74; 203/91; 203/87; 203/DIG. 21; 260/603 C; 562/536
[58] Field of Search .............. 203/15, 62, 63, 42, 203/39, 87, DIG. 21, 91, 74; 260/530 N, 526 N, 603 C, 560, 212

[56] References Cited
U.S. PATENT DOCUMENTS

| | | | |
|---|---|---|---|
| 2,811,545 | 10/1957 | Steadman | 560/212 |
| 2,922,815 | 1/1960 | Faerber | 260/526 N |
| 3,414,485 | 12/1968 | Speed | 260/526 N |
| 3,926,744 | 12/1975 | Noll et al. | 203/55 |
| 3,932,500 | 1/1976 | Duembgen et al. | 260/526 N |
| 4,001,316 | 1/1977 | Ishimi | 260/530 N |
| 4,012,449 | 3/1977 | Shakakura et al. | 260/603 R |

Primary Examiner—Wilbur L. Bascomb, Jr.
Attorney, Agent, or Firm—William C. Long; David Dick; Harold N. Wells

[57] ABSTRACT

In an oxidation process for converting methacrolein to methacrylic acid, methacrylic acid is recovered by cooling and condensing the effluent from the oxidation, followed by azeotropic distillation of the condensate with a suitable solvent, such as methyl n-propyl ketone. The condensed effluent contains methacrylic acid and water as the major components along with by-product acetic acid, a minor amount of unreacted methacrolein and impurities. Substantially dry crude methacrylic acid is separated as a bottom product from the azeotropic distillation and an azeotrope of water and the solvent is taken overhead and condensed. After condensation, solvent-rich and water-rich phases form and are separated. The solvent-rich phase is returned to the distillation column as a reflux, while the water-rich phase is sent to a stripping column for recovery of residual solvent. Water is withdrawn from the bottom of the stripping column and recycled or discarded, as desired. Optionally, an additional distillation column may be used in order to remove unreacted methacrolein from the solvent used in the azeotropic distillation.

12 Claims, 2 Drawing Figures

PROCESS FOR RECOVERING METHACRYLIC ACID

PRIOR ART

The present invention relates in general to processes for production of methacrylic acid from methacrolein by oxidation. In particular, the invention relates to a two-step oxidation process in which a feed stock comprising isobutylene and/or tertiary butyl alcohol is oxidized first to methacrolein and thereafter to methacrylic acid, with both steps being carried out at a temperature in the range of 270°–500° C. in presence of molecular oxygen over a catalyst. Such processes are known generally in the art. An example is U.S. Pat. No. 4,012,449, disclosing a process and a catalyst for the production of methacrolein from isobutylene and/or tertiary butyl alcohol. The second step on which methacrolein is oxidized to methacrylic acid is disclosed and claimed in U.S. Pat. No. 4,001,316.

In addition to the two-step oxidation of isobutylene and/or tertiary butyl alcohol to methacrolein and then to methacrylic acid, there are other processes for production of methacrylic acid from the same feed stocks. One such prior art process, which will be referred to subsequently, is the process disclosed by Escambia Chemical Corporation. Their patents show that isobutylene may be oxidized over a catalyst in the presence of nitric acid, and, preferably, dinitrogen tetroxide to form alpha hydroxy isobutyric acid. (U.S. Pat. Nos. 2,847,453 and 2,847,465), which is then dehydrated in the presence of a catalyst to form methacrylic acid (U.S. Pat. Nos. 2,811,545 and 3,562,230).

In the two-step process for oxidation of isobutylene and/or tertiary butyl alcohol to methacrylic acid, the effluent from the second oxidation step contains methacrylic acid and water as principal constituents, along with unreacted methacrolein and by-product acetic acid and impurities. The methacrylic acid typically will be a relatively small portion, less than 5 mol% of the total effluent stream, since substantial quantities of stream and inert gases are used in the process. For most uses, the methacrylic acid must be separated from the water, but recovery of methacrylic acid is difficult, since it forms an azeotrope with water.

One possible approach to obtaining essentially dry methacrylic acid would be to cool and condense the methacrolein oxidation reactor effluent to separate the inert gases from the methacrylic acid and water and then to distill the liquid mixture to obtain essentially dry methacrylic acid. Since water and methacrylic acid form an azeotrope containing about 23% by weight of the acid (at 760 mm Hg), it will be appreciated that such a distillation process will produce a substantial stream of methacrylic acid in water, which would be recycled to the oxidation step to recover the acid. This could result in losses of methacrylic acid to the lower acids. Consequently, a more efficient method of separation than simple distillation would be preferred.

At least three other methods might be considered for the recovery of methacrylic acid from gaseous mixtures containing substantial amounts of water. The first such method is scrubbing of the methacrylic acid from the hot reactor effluent gas with solvents, while leaving the bulk of the water in the gaseous effluent. In the second and third methods, the methacrylic acid and water are condensed and then treated with solvents to separate the acid from the water. In the second method, inorganic salts are introduced into a liquid mixture of solvent, acid and water in order to form a saltwater phase which can be easily separated and which contains little acid or solvent. The methacrylic acid would then be recovered from the solvent and any residual water by azeotropic distillation. In the third method, methacrylic acid is extracted with solvents from an acid-water mixture but without the use of salts to assist the separation. The water is removed as a separate phase and methacrylic acid is separated from the solvent and the residual water by azeotropic distillation.

The first process may be illustrated by U.S. Pat. No. 3,926,744 issued to Noll et al., and 3,932,500 issued Duembgen, et al., which relate to the recovery of acrylic acid (rather than methacrylic acid) from water. In both patents, the effluent from the acrolein oxidation step is introduced into a scrubber while still in the vapor phase in order to selectively remove acrylic acid.

Duembgen scrubs the reactor effluent with extremely hydrophobic solvents, such as paraffin hydrocarbons, diphenyl, and diphenyl ether under conditions which are established to minimize the amount of water removed from the gaseous stream. What water is removed is immediately stripped from the solvent-acid mixture in a desorbing column and returned to the scrubber. The stripped solvent-acid mixture is distilled to separate acrylic acid from the solvent.

Noll scrubs the hot reactor effluent gases in two stages with a mixture of solvent and water. The temperature in the first stage is kept relatively high and the quantities of solvent and water are adjusted to minimize the collection of water along with the acrylic acid. This permits distillation of acrylic acid directly from the solvent to produce acrylic acid. Noll suggests as solvents, monovalent aliphatic alcohols and the acetic acid esters or acrylic acid esters of such alcohols.

A second potential method of recovery of methacrylic acid, that is, by introducing inorganic salts for assisting in removal of water, may be illustrated by U.S. Pat. No. 2,922,815, issued to Faerber, who disclosed the technique as used for recovery of acrylic acid (rather than methacrylic acid). Faerber mentions that metal salts have been used alone to separate water from acrylic acid and discloses a process which employs nickel salts along with a ketone (e.g. methyl ethyl ketone, methyl propyl ketone, methyl isopropyl ketone, diethyl ketone, ethyl isopropyl ketone, and di isopropyl ketone) to carry out the separation of acrylic acid. The nickel salts form a salt-water layer which is substantially free of acrylic acid and which can be easily separated. Acrylic acid remains with the ketone-rich phase and may be separated by the azeotropic distillation. The introduction of nickel salts creates processing difficulties since they must be separated from the acrylic acid and any recycled streams. A simpler process clearly would be preferred.

The third potential recovery method may be illustrated by U.S. Pat. No. 3,986,153 issued to Ohrui, et al. Ohrui does not disclose a complete process for recovery of methacrylic or acrylic acids, but only discusses the optimization of a mixture of solvents consisting of methyl ethyl ketone and a xylene or ethyl benzene and shows that by optimizing the solvent composition, the distribution coefficient of the acid can be maximized. An aqueous solution of acid would be extracted by the optimized solvent system and the resulting acid-solvent mixture recovered by distillation or other conventional techniques.

Another example of the third method is given in U.S. Pat. No. 3,414,485 issued to Speed. Speed was particularly concerned with the preparation of methacrylic acid from a process previously mentioned, in which methacrylic acid is formed by catalytic dehydration of alpha hydroxy isobutyric acid. Speed states that the impurities carried over from the synthesis of methacrylic acid initiate polymerization of the methacrylic acid, and that azeotropic distillation was found to be inoperable due to excessive polymerization unless a preliminary extraction step was used. Polymerization was said to occur even if inhibitors were used. Consequently, Speed found it necessary to remove the troublesome impurities by extraction of crude methacrylic acid with a solvent. After condensing the dehydration reactor product to form a crude wet methacrylic acid, Speed extracted methacrylic acid with a solvent, e.g. xylene, toluene, n-octane, m-chlorobenzene, methyl amyl ketone, ligroin and methyl methacrylate. After settling, a water phase was separated from the acid-solvent mixture. Removal of polymerization initiators along with the water phase containing them allowed Speed to use azeotropic distillation for recovery of the methacrylic acid from the solvent and any small amount of residual water.

It has been found that when methacrylic acid is formed via processes involving the oxidation of methacrolein, that the preliminary extraction of crude methacrylic acid by solvents is not required. Particularly in connection with the two-step oxidation process by which isobutylene and/or tertiary butyl alcohol are converted into methacrylic acid, a recovery process requiring no solvent extraction step may be used, as will be described more fully hereafter.

SUMMARY OF THE INVENTION

In one aspect, the invention comprises a process for the recovery of methacrylic acid produced by the catalytic oxidation of methacrolein to methacrylic acid. The gaseous effluent from the oxidation reaction is cooled and methacrylic acid, by-product acetic acid, any unreacted methacrolein, water, and impurities are condensed and the condensate azeotropically distilled with a suitable solvent. The solvent is selected from the group consisting of methyl n-propyl ketone, methyl ethyl ketone, methyl isobutyl ketone, methyl isopropyl ketone, ethyl isopropyl ketone, diethyl ketone, ethyl tertiary amyl ether, methyl tertiary amyl ether, n-propyl ether and mixtures thereof. Preferably, methyl n-propyl ketone is used.

In another aspect, the invention comprises a process for the recovery of methacrylic acid and acetic acid produced by the oxidation of isobutylene or tertiary butyl alcohol into methacrolein, followed by the recovery of methacrolein, and thereafter oxidation of the methacrolein to form methacrylic acid. The methacrylic acid and acetic acid are recovered by cooling and condensing the effluent from the second oxidation (of methacrolein) and then passing the condensed effluent directly, and without preliminary extraction, into an azeotropic distillation carried out in the presence of a solvent, preferably methyl n-propyl ketone. Substantially dry crude methacrylic acid is withdrawn as a bottoms product from the azeotropic distillation, along with impurities and acetic acid. Separation and recovery of methacrylic acid and acetic acid may be carried out in conventional distillation facilities.

In a preferred embodiment, the gaseous effluent is cooled and condensed by direct contact with a recirculating liquid stream comprising condensed effluent. A portion of the recirculating liquid stream is withdrawn and passed directly, and without preliminary solvent extraction, to an azeotropic distillation which is carried out in the presence of methyl n-propyl ketone. The overhead product from the azeotropic distillation is an azeotrope of the solvent and water which is condensed and separated into two liquid layers. The solvent-rich layer is returned to the distillation as reflux, the water-rich layer is passed to a stripping column for removal of residual solvent. The bottom product from the azeotropic distillation is essentially dry methacrylic acid containing impurities and acetic acid, which can be separated in conventional facilities. Optionally, unreacted methacrolein may be removed by distilling a portion of the solvent-rich layer.

DESCRIPTION OF PREFERRED EMBODIMENTS

Figure 1:
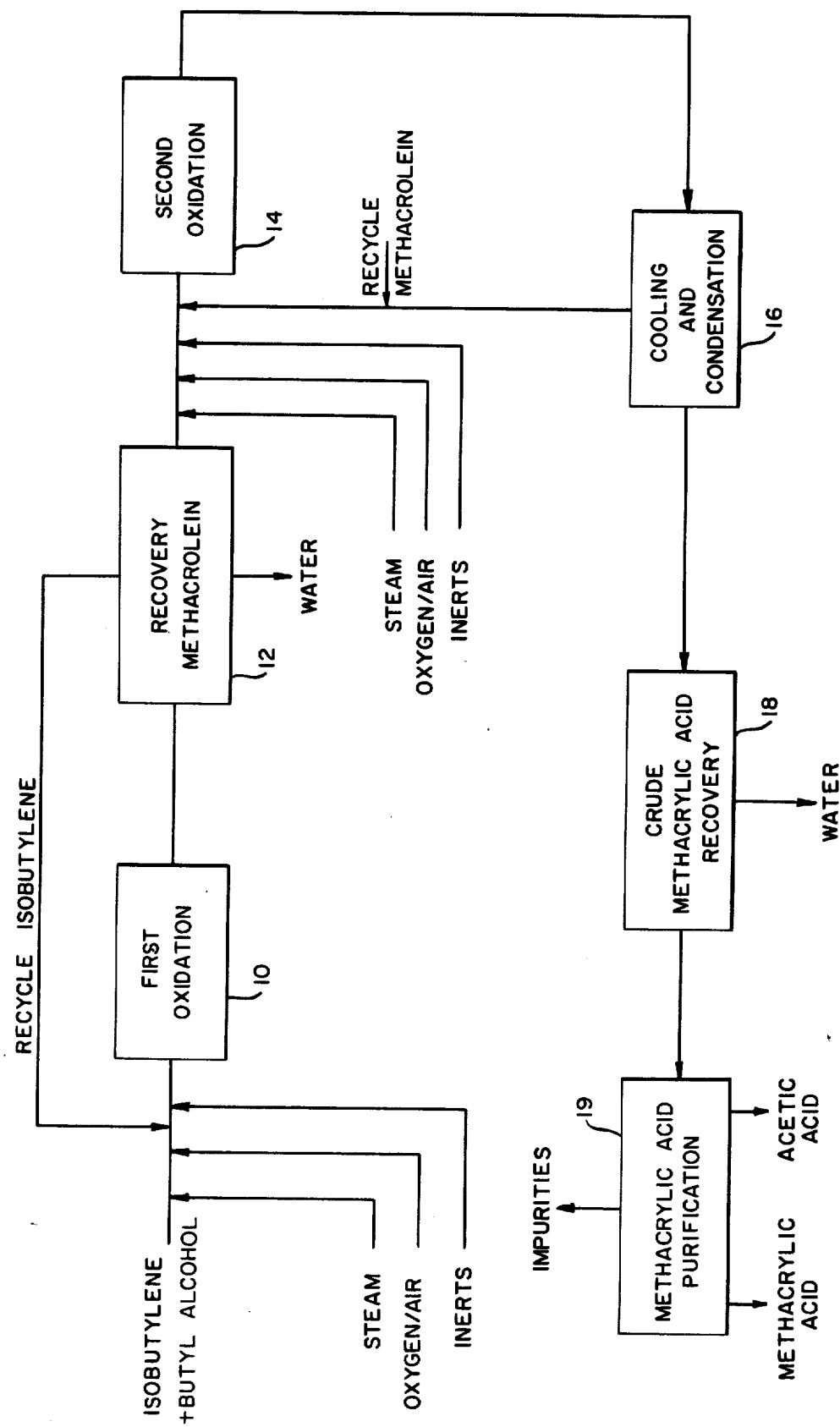
FIG. 1 is a block diagram showing the two-step oxidation of isobutylene and/or tertiary butyl alcohol to methacrylic acid and the recovery process of the invention.

FIG. 1 shows in a block diagram the two-step oxidation is isobutylene and/or tertiary butyl alcohol to methacrylic acid. Isobutylene and/or tertiary butyl alcohol are introduced, along with molecular oxygen, which may be in the form of air, into a first oxidation step 10 for conversion to methacrolein in the presence of a suitable catalyst. Substantial quantities of water vapor and nitrogen typically are present in the reactor. They are shown in the diagram as being added to the oxidation step 10, however, depending upon the design selected, they may not necessarily be added as such. Nitrogen usually enters with the air supply and if that is the case, nitrogen must be purged to maintain the desired amount in the oxidation reaction. Although water is produced in the oxidation reaction, still larger amounts are used and it may be added directly as steam or indirectly through adjustments of the water content of the recycle gas stream. The reaction typically is carried out at a temperature in the range of about 330°–500° C., and at a pressure of up to about 14 kg/cm² gauge, over a catalyst typically comprising a mixture of base metal oxides. Since the reaction is highly exothermic, the catalyst is often placed inside small diameter tubes and the heat of reaction removed by circulating a molten salt on the outside of the tubes.

Methacrolein is recovered and purified in recovery process 12 between the two oxidation steps, 10 and 14. Unreacted isobutylene separated during the recovery of methacrolein could be recycled to the first step oxidation as shown in the diagram.

After recovery, the methacrolein may be fed to the second oxidation step 14 where the methacrolein is oxidized by molecular oxygen to methacrylic acid in the presence of substantial amounts of water vapor and nitrogen at temperatures typically in the range of 270°–450° C. and at pressures up to about 7 kg/cm² gauge, over a mixed base metal oxide catalyst. The comments made previously with regard to the direct introduction of steam and inerts apply to this second oxidation step also. That is, they may be added as such, but need not necessarily be, depending upon the design selected.

The present invention is particularly concerned with improvement in the recovery of methacrylic acid from the second oxidation step 14. The recovery process is shown generally in FIG. 1 to consist of a cooling and condensation step 16, including separation of gases for recycle to the second oxidation stage and followed immediately, and without a solvent extraction step, by recovery of the crude methacrylic acid 18 by azeotropic distillation in the presence of a suitable solvent, followed by purification of the crude methacrylic acid. The recovery process is shown in more detail in FIG. 2, but in general the process produces methacrylic acid, acetic acid, and by product impurities as shown.

Figure 2:
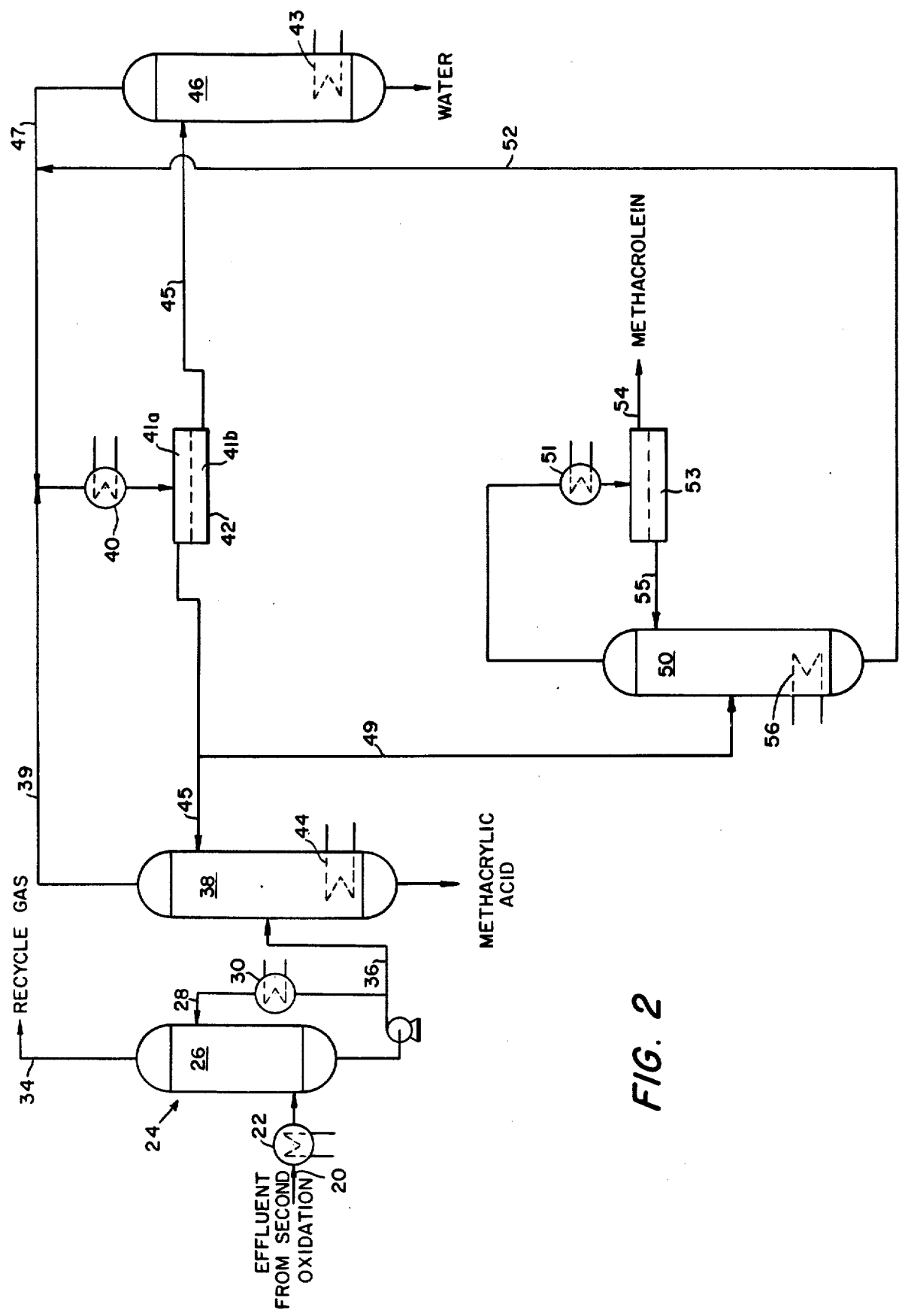
FIG. 2 shows the process for recovery of methacrylic acid from the effluent of the second oxidation step.

The cooling and condensing of hot effluent gases from the second oxidation step may be carried out as shown in FIG. 2, although alternative means will occur to those skilled in the art. In the embodiment of FIG. 2, the effluent typically leaves the second (methacrolein) oxidation step 14 via line 20 at a temperature of about 290°–325° C. and a low pressure of about 0.25 kg/cm² gauge. It may be passed through indirect heat exchange 22 to cool the effluent gases and to recover the reaction heat, such as by generating steam. Leaving heat exchanger 22, the temperature would typically be about 150° C. upstream of the subsequent quenching step 24, but it will be understood by those skilled in the art that the temperature of the effluent gases after indirect heat exchanger 22 is not critical, but may be adjusted to achieve an optimum equipment design for both the indirect heat exchange and direct quenching steps. At a temperature of about 150° C., the effluent stream remains in the gaseous form as it enters the quench tower 26. It is contacted there by a recirculating liquid stream which is introduced at the top of tower 26 through line 28. The liquid stream is derived by cooling and partial condensation of the gases to a suitable temperature, say about 40° C. The two major constituents, that is, methacrylic acid and water are accompanied by unreacted methacrolein, by-product acetic acid and impurities. Quench tower 26 is provided with suitable means for contacting the upwardly flowing effluent gases with the liquid quench stream, such as packing of various types and gas-liquid contacting trays which are familiar to those skilled in the art.

As the effluent gases rise in the quench tower 26, heat is removed by direct contact with the liquid quench stream and water, methacrylic acid and acetic acid are condensed along with smaller amounts of impurities. The heat acquired by the quench stream is removed by indirect heat exchange in exchanger 30, which will ordinarily employ cooling water or air at ambient temperature. The liquid leaving the quench tower 26 is recirculated through exchanger 30 and returned to the tower 26 via line 28. The temperature of the recirculating steam entering the quench tower 26 may be selected to optimize the recovery of methacrylic acid, while minimizing the size and operating costs of the equipment involved. Gases exiting the quench tower 26 are returned via line 34 to the second oxidation step (14 in FIG. 1) in order to avoid losses of valuable materials such as methacrolein carried overhead from the quench tower 26 and to minimize makeup of gases to the first oxidation step.

The net production of methacrylic acid, acetic acid, and water, along with unreacted methacrolein and impurities such as acrylic acid, is passed via line 36 to the azeotropic distillation colume 38. Column 38 is provided with suitable means for contacting the gas and liquid streams circulating within the column and may employ packing, trays and the like for this purpose. The column is operated at sub-atmospheric pressure, preferably between 50 and 325 mm Hg absolute and in the presence of a suitable solvent. In general, the solvents will have a boiling point lower than that of methacrylic acid and will form an azeotrope with water capable of being efficiently condensed by ambient temperature coolants. When acetic acid is to be recovered as a by-product, the solvent should not carry acetic acid overhead. If it is withdrawn with the methacrylic acid from the bottom of the column, the acetic acid may be recovered by distillation. Suitable solvents include methyl n-propyl ketone, methyl ethyl ketone, methyl isobutyl ketone, methyl isopropyl ketone, diethyl ketone, ethyl isopropyl ketone, ethyl tertiary amyl ether, methyl tertiary amyl ether, n-propyl ether and mixtures thereof. Methyl n-propyl ketone is preferred. Other solvents could be used if refrigeration were available to condense the overhead gases from the azeotropic distillation or if the recovery of acetic acid was not desired.

The solvent recirculates through the upper portion of the column 38 and the overhead equipment, that is, condenser 40 and separator 42. Heat is applied to the bottom of the column 38 by a conventional reboiler 44, and heat is removed by overhead condenser 40. Essentially water-free methacrylic acid, that is, containing less than 0.1 mol percent water, may be withdrawn at the bottom of the column. The acid contains substantially only the by-products, principally acetic acid, and other impurities such as acrylic acid. Water and the solvent leave the top of the column as an azeotropic mixture. The amount of solvent required thus is determined by the amount of water to be taken overhead. The mixture is condensed and cooled in condenser 40 to a temperature determined by the coolant available, typically about 40° C. if an ambient temperature coolant is used. At such a temperature, the solvent-water azeotropic mixture is immiscible and separates into two liquid layers, a solvent-rich layer 41a and a water-rich layer 41b. All of the solvent-rich layer, which contains only a small proportion of dissolved water, is returned to the column via line 45 as a reflux stream. The solvent recirculates through the tower and overhead equipment and is not withdrawn with a product stream. The water-rich layer 41b, containing a small amount of solvent, passes via line 45 to a stripping column 46, which is operated so as to recover the solvent portion and to return it as overhead stream 47 to mix with the overhead vapor from the azeotropic distillation column 38. Heat is supplied to stripper 46 by a conventional reboiler 43.

Methacrylic acid withdrawn from the bottom of the azeotropic distillation column 38 contains impurities and may be sent to conventional distillation facilities for further purification, if required. Since by-product acetic acid is present in significant quantity, it may be fractionated from the crude methacrylic acid for use or sale.

Inasmuch as any unreacted methacrolein passes overhead in the azeotropic distillation column 38 and is removed from the water layer 41b by the stripping column 46, the methacrolein will tend to concentrate in the upper portion of the azeotropic distillation column 38 and its overhead facilities. Consequently, in order to remove the methacrolein, a purge stream may be taken from the solvent-rich phase 41a, either intermittently or continuously. This stream 49 could be disposed of or, optionally, could be recovered in a distillation column such as is designated 50 in FIG. 2. The bottom of column 50 would produce solvent essentially free of methacrolein for return to the azeotropic distillation column 38 via line 52, while methacrolein would be recovered overhead and returned to the second stage oxidation via line 54. Water and methacrolein would pass overhead from column 50, and after being condensed in condenser 51, would be collected in separator 53 where two layers would form, one rich in methacrolein and the other rich in water. The water-rich layer would be returned as reflux via line 55 to the column 50 and only the methacrolein-containing layer removed. Alternatively, a portion of the methacrolein layer could be returned as reflux. Heat would be supplied to column 50 by reboiler 56. As with the other columns previously described, column 38 would be provided with packing, trays, or other suitable internal means for contacting gases and liquids.

It will be understood by those skilled in the art that inhibitors, such as hydroquinone, are commonly used to prevent polymerization of the aldehydes and acids during the recovery process.

In a specific example of the process of the invention according to FIG. 2, an effluent from the second oxidation step is cooled by indirect heat exchange 22 to a temperature of about 150° C. and thereafter passed into quench tower 26 and cooled further by direct contact with a recirculating liquid stream of condensed effluent so that the recycled gases leaving the top of column 26 are at a temperature of about 40° C. The recycled gas stream contains principally nitrogen, water vapor, unreacted methacrolein, and minor amounts of by-products and impurities. The recirculating quench stream 28 and the slip stream 36 sent to column 38, each contain about 44 mol% methacrylic acid, about 51 mol% water, about 5 mol% acetic acid, about 0.5 mol% of other impurities expressed as acrylic acid, and less than 0.2 mol% methacrolein. About 1000 mols/hr of condensate are fed to tower 38 via line 36. About 492 mols/hr are withdrawn as crude methacrylic acid from the bottom of the column, which includes essentially all of the entering methacrylic acid, acetic acid and acrylic acid and contains less than 0.1 mol percent water. The column operates below atmospheric pressure, say about 100 mm of mercury absolute at the overhead separator, although a pressure between 75 and 325 mm of mercury absolute may be used. At lower pressures refrigeration would ordinarily be necessary to condense the overhead gases and at higher pressures polymerization of the bottom liquid would be excessive. The overhead stream (line 39) contains about 1144 mols/hr of an azeotropic mixture of water and methyl n-propyl ketone, typically about 53.8 mol% water and about 46.2 mol% ketone, and varying somewhat with the pressure of the column. The overhead stream is cooled and condensed and enters separator 42 at about 40° C. The ketone-rich layer, 41a, will contain about 83 mol% ketone and about 17 mol% water. It is not withdrawn but is returned entirely to column 38 as reflux at a rate of about 638 mols/hr. The water-rich layer, 41b, which is to be disposed of through the stripping column 46, will contain approximately 99.2 mol% water and 0.8 mol% methyl n-propyl ketone and in this example will have a rate of about 529 mols/hr. After stripping, about 507 mols/hr of water will be removed from the bottom of the stripping column 46 at a temperature of about 70° C. or as otherwise determined by the column pressure, while all of the ketone (about 4 mols/hr) will be removed as an overhead product along with about 17 mols/hr of water and returned to the azeotropic distillation column 38. The water stripping column 46 will be operated at a suitable sub-atmospheric pressure which will permit return of the overhead vapors to the azeotropic distillation column 38.

A purge stream may be removed from the reflux to the azeotropic distillation column (line 49 in FIG. 2). The flow rate of the purge stream will be adjusted so that it contains an amount of methacrolein equivalent to that entering the methacrylic acid recovery system, or about 2 mols/hr in this example. It will carry with it an equilibrium amount of solvent and water from separator 42 (about 33 mols/hr ketone and 7 mols/hr water in this example). The methacrolein recovery column 50 may be operated at essentially atmospheric pressure. About 40 mols/hr of solvent-water azeotrope containing about 82 mol% methyl isopropyl ketone is returned to the azeotropic distillation column 38 via line 52. After condensation of the overhead vapor in exchanger 51 and cooling to about 40° C., the methacrolein will separate in separator 53 as a layer above the bulk of condensed water and may be withdrawn for return to the second oxidation step.

As a second example of the process of the invention, methyl isopropyl ketone is used as the solvent in the azeotropic distillation, rather than the preferred methyl n-propyl ketone. Since the azeotropic composition of methyl isopropyl ketone and water differs from that of methyl n-propyl ketone and water, the quantities circulated through the overhead equipment will vary as required by the variation in composition.

The azeotrope of methyl isopropyl ketone and water contains a larger proportion of ketone than the corresponding azeotrope of methyl n-propyl ketone. Thus, the amount of solvent circulation is increased relative to the previous example, since the amount of solvent is selected which azeotropes with the water to be removed. Also, the compositions of the water-rich and ketone-rich layers in the overhead separator are also changed with methyl isopropyl ketone is used. In particular, more ketone is contained in the water-rich layer than is the case for methyl isopropyl ketone, thereby increasing the load on the stripping column.

For purposes of this example, it will be assumed that the composition of the stream entering the azeotropic distillation column 38 is the same as in previous examples, and that the temperature is again about 40° C. The column is operated at a pressure of about 150 mm mercury absolute measured at the overhead separator. As in the previous example, about 1,000 mols/hr are fed to tower 38, and 492 mols/hr of crude methacrylic acid are withdrawn from the bottom of column 38 for further purification. The flow rates in the overhead equipment are different, as will be seen from the following description.

The overhead stream (line 39) contains about 1565 mols/hr of an azeotrope mixture of water and methyl isopropyl ketone having a composition of about 41.9 mol% water and about 58.1 mol% ketone. After being cooled and condensed in overhead condenser 40, the overhead stream enters separator 42 at about 40° C. Two layers form, 41a, and 41b. Layer 41a is ketone rich containing about 85.8 mol% ketone and about 14.2 mol% water. It is returned entirely to column 38 as reflux (1059 mols/hr), except for a small slip stream removed for purge of methacrolein.

Layer 41b is water rich containing about 98.9 mol% water and about 1.1 mol% methyl isopropyl ketone. It is withdrawn entirely (536 mols/hr) and passed to a water stripping column 46 where the methyl isopropyl ketone (5.8 mols/hr) is removed and returned with an equilibrium amount of water to the overhead condenser. The water entering the column 38 is withdrawn from the bottom of column 46, essentially solvent-free, as in the previous example in an amount of 506 mols/hr. As in the previous example, a slip stream may be removed from the reflux to column 38 to recover methacrolein as shown in column 50, as a purge to prevent the build up of overhead in tower 38.

The foregoing description of the preferred embodiments of the invention is intended for illustration only and should not be considered as limiting the scope of the invention which is defined by claims which follow.

What is claimed is:

1. In a process for the preparation of methacrylic acid by the vapor phase catalytic oxidation of methacrolein in the presence of molecular oxygen, water vapor, and inert gases, the recovery of methacrylic acid from the effluent vapors from said oxidation by: (a) cooling and condensing said effluent to a pre-determined temperature and thereby forming a vapor portion comprising substantially unreacted methacrolein and inert gases and a liquid portion comprising substantially methacrylic acid, acetic acid, water, a minor amount of unreacted methacrolein, and impurities; (b) separating said liquid portion of (a) from said vapor portion of (a) and azeotropically distilling at a sub-atmospheric pressure said liquid portion in the presence of a solvent selected from the group consisting of methyl n-propyl ketone, methyl ethyl ketone, methyl isobutyl ketone, methyl isopropyl ketone, diethyl ketone, ethyl isopropyl ketone, ethyl tertiary amyl ether, methyl tertiary amyl ether, n-propyl ether, and mixtures thereof, the overhead product from said distillation comprising substantially an azeotrope of said solvent and water and a minor amount of unreacted methacrolein and the bottom product therefrom being substantially free of water and comprising said methacrylic acid, acetic acid, and impurities.

2. The process of claim 1 wherein said azeotropic distillation is carried out at a pressure of between 50 and 325 mm Hg absolute.

3. The process of claim 1 wherein said solvent is methyl n-propyl ketone.

4. The process of claim 1 wherein and cooling and condensing of (a) comprises the steps of (i) cooling said effluent and recovering heat therefrom and thereafter (ii) quenching said cooled effluent of (i) by directly contacting said effluent with a liquid stream comprising condensed effluent, and (iii) withdrawing a liquid portion of the condensed effluent stream of (ii) equivalent in quantity to said liquid portion (a).

5. The process of claim 1 further comprising the steps of condensing and cooling the azeotrope of (b), separating said cooled azeotrope to form a solvent-rich layer and water-rich layer, and stripping said water-rich layer to remove the solvent content thereof.

6. The process of claim 5 further comprising the step of removing a portion of said solvent-rich layer and distilling said portion to remove the methacrolein content thereof.

7. The process of claim 1 wherein said methacrolein is prepared by catalytic oxidation of isobutylene and/or tertiary butyl alcohol.

8. A process for preparation of methacrylic acid comprising: (a) in a first oxidation step, oxidizing in the presence of a catalyst a gaseous feed stream containing isobutylene or t-butyl alcohol or mixtures thereof and molecular oxygen, water vapor, and inert gases to form methacrolein; (b) recovering the methacrolein from the effluent gases of said first oxidation step of (a); (c) in a second oxidation step, oxidizing in the presence of a catalyst the recovered methacrolein of (b) in a gas phase reaction in the presence of molecular oxygen, water vapor, and inert gases to form methacrylic acid; the improvement comprising (d) cooling the effluent gases of said second oxidation step of (c) and recovering heat therefrom; (e) cooling, and condensing said cooled effluent gases of (d) by directly contacting said effluent gases with a liquid stream comprising condensed effluent; (f) withdrawing a portion of the condensed liquid stream of (e) containing substantially all of the methacrylic acid formed in (c) and acetic acid, water, a minor amount of unreacted methacrolein, and impurities; and (g) azeotropically distilling under a sub-atmospheric pressure said liquid portion of (f) in the presence of a solvent selected from the group consisting of methyl n-propyl ketone, methyl ethyl ketone, methyl isobutyl ketone, methyl isopropyl ketone, diethyl ketone, ethyl isopropyl ketone, ethyl tertiary amyl ether, methyl tertiary amyl ether, n-propyl ether, and mixtures thereof, the overhead product from said distillation comprising substantially an azeotrope of said solvent and water and a minor amount of unreacted methacrolein and the bottom product therefrom being substantially free of water and comprising said methacrylic acid.

9. The process of claim 8 wherein said azeotropic distillation is carried out at a pressure of between 50 and 325 mm Hg absolute.

10. The process of claim 8 wherein said solvent is methyl n-propyl ketone.

11. The process of claim 8 further comprising the steps of condensing and cooling the azeotrope of (g), separating said cooled azeotrope to form a solvent-rich layer and water-rich layer, and stripping said water-rich layer to remove the solvent content thereof.

12. The process of claim 11 further comprising the step of removing a portion of said solvent-rich layer and distilling said portion to remove the methacrolein content thereof.

* * * * *